(12) United States Patent
Huang

(10) Patent No.: US 8,790,683 B2
(45) Date of Patent: Jul. 29, 2014

(54) CELL TISSUE GEL CONTAINING COLLAGEN AND HYALURONAN

(75) Inventor: Lynn L. H. Huang, Tainan (TW)

(73) Assignee: National Cheng Kung University, Tainan (TW)

( * ) Notice: Subject to any disclaimer, the term of this patent is extended or adjusted under 35 U.S.C. 154(b) by 285 days.

(21) Appl. No.: 12/974,535

(22) Filed: Dec. 21, 2010

(65) Prior Publication Data

US 2011/0150823 A1 Jun. 23, 2011

Related U.S. Application Data

(60) Provisional application No. 61/289,132, filed on Dec. 22, 2009.

(51) Int. Cl.

| | |
|---|---|
| *A61F 2/00* | (2006.01) |
| *A01N 63/00* | (2006.01) |
| *A01N 65/00* | (2009.01) |
| *C12N 11/00* | (2006.01) |
| *C12N 5/02* | (2006.01) |
| *A61L 27/26* | (2006.01) |
| *C08L 5/08* | (2006.01) |
| *A61K 35/28* | (2006.01) |
| *A61K 35/50* | (2006.01) |

(52) U.S. Cl.
CPC . *A61L 27/26* (2013.01); *C08L 5/08* (2013.01); *A61K 35/28* (2013.01); *A61K 35/50* (2013.01)
USPC ........... 424/426; 424/93.1; 435/174; 435/397

(58) Field of Classification Search
CPC ........... A61L 27/26; C08L 5/08; C08L 89/06; A61K 35/28; A61K 35/50
USPC .......................... 424/426, 93.1; 435/174, 397
See application file for complete search history.

(56) References Cited

U.S. PATENT DOCUMENTS

| | | | |
|---|---|---|---|
| 6,773,723 B1 * | 8/2004 | Spiro et al. ..................... | 424/488 |
| 2005/0113937 A1 | 5/2005 | Binette et al. | |
| 2006/0018946 A1 | 1/2006 | Prescott | |
| 2006/0233850 A1 | 10/2006 | Michal | |
| 2007/0116680 A1 | 5/2007 | Stegemann et al. | |
| 2009/0076624 A1 | 3/2009 | Rahaman et al. | |
| 2009/0093755 A1 | 4/2009 | Schroeder et al. | |
| 2009/0098110 A1 * | 4/2009 | Adams et al. ............. | 424/130.1 |
| 2009/0305415 A1 | 12/2009 | Huang | |
| 2009/0305416 A1 | 12/2009 | Huang | |

FOREIGN PATENT DOCUMENTS

WO        02/17713        3/2002

OTHER PUBLICATIONS

Hogan et al., Hyaluronic acid: a natural biopolymer with a broad range of biomedical and industrial applications Biotechnol Lett (2007) 29:17-25.*
Bellows et al Dev Biol. May 1989;133(1):8-13.Determination of numbers of osteoprogenitors present in isolated fetal rat calvaria cells in vitro. Abstract.*
Liu et al Tissue Eng. Dec. 2006;12(12):3405-16. Osteochondral defect repair with autologous bone marrow-derived mesenchymal stem cells in an injectable, in situ, cross-linked synthetic extracellular matrix.*
Angele et al., Engineering of osteochondral tissue with bone marrow mesenchymal progenitor cells in a derivatized hyaluronan-gelatin composite sponge Tissue Eng Dec. 1999;5(6):545-54.*
Noth, et al. "Crondrogenic differentiation of human msxenchymal stem cells in collagen type I hydrogels" Journal of Biomedical Materials Research part A. (2007) pp. 626-635.
Crevensten, G., et al. "Intervertebral Disc Cell Therapy for Regeneration: Mesenchymal Stem Cell Implantation in Rat Intervertebral Discs" Annals of Biomedical Engineering (2004) pp. 430-434.
Lee, K. Y., et al. "Hydrogels for Tissue Engineering" Chemical Reviews (2001) pp. 1869-1879.
C. M. Liu, et al. "Hualuronan substratum holds mesenchymal stem cells at a slow-cycling status" Cell and Tissue Research (2008) 9 pages.
Yan, Jinglian, et al. "Recovery from hind limb ischemia in less effective in type 2 than type 1 diabetic mice: Roles of endothelial nitric oxide synthase and endothelial progenitor cells" Journal of Vascular Surgery (2009) pp. 1-11.
Pardue, Erin L., et al. "Role of hyaluronan in angiogenesis and its utility to angiogenic tissue engineering" Organogenesis vol. 4, issue 4 (Oct./Nov./Dec. 2008) pp. 203-214.
Lui, Chi-Mou, et al. "Hyaluronan substratum induces multidrug resistance in human mesenchymal stem cells via DC44 signaling" Cell Tissue Res. (Feb. 21, 2009) 11 pages.

* cited by examiner

*Primary Examiner* — Maria Leavitt
(74) *Attorney, Agent, or Firm* — Cesari and McKenna, LLP

(57) ABSTRACT

A cell tissue gel containing collagen and hyaluronan at a weight ratio of 0.01-100:1 and uses thereof for stem cell delivery.

9 Claims, No Drawings

CELL TISSUE GEL CONTAINING COLLAGEN AND HYALURONAN

CROSS-REFERENCE TO RELATED APPLICATIONS

This application claims priority to U.S. Provisional Patent Application Ser. No. 61/289,132, filed on Dec. 22, 2009, the content of which is hereby incorporated by reference in its entirety.

BACKGROUND OF THE INVENTION

Stem cell therapy is a promising approach in treating degenerative diseases. However, it remains challenging to retain stem cells at an implantation site and maintain their viability in a recipient so as to effect tissue repair. There is a need for a vehicle (e.g., a cell tissue gel) that facilitates site-specific stem cell implantation with high cell viability.

SUMMARY OF THE INVENTION

The present invention is based on an unexpected discovery that stem cells display improved viability when growing in a cell tissue gel that contains collagen and hyaluronan at particular weight ratios, a cell growth medium, and optionally gelatin.

Accordingly, this invention features a cell tissue gel containing collagen and hyaluronan at a weight ratio of 0.01-100 (collagen):1 (hyaluronan). The concentration of the hyaluronan can be 0.001 to 100 mg/ml (e.g., 0.01 to 1 mg/ml) and that of the collagen can be 0.001 to 100 mg/ml. Preferably, the collagen concentration is 0.1 to 100 mg/ml and the hyaluronan concentration is 0.01 to 35 mg/ml. More preferably, the collagen concentration is 3-40 mg/ml (e.g., 6 mg/ml or 9 mg/ml) and the hyaluronan concentration is 0.2-20 mg/ml.

The cell tissue gel of this invention can further contain a nutrient for cell growth (e.g., a cell culture medium), a bioactive agent, one or more matrix factors, and/or stem cells. The bioactive agent can be a growth factor, e.g., epidermal growth factor, fibroblast growth factor, vascular endothelial growth factor, connective tissue growth factor, platelet-derived growth factor, insulin-like growth factor, nerve growth factor, hepatocyte growth factor, colony-stimulating factor, stem cell factor, keratinocyte growth factor, granulocyte colony-stimulating factor, gramulocyte macrophase colony-stimulating factor, glial derived neurotrophic factor, ciliary neurotrophic factor, endothelial-monocyte activating polypeptide, epithelial neutrophil activating peptide, erythropoietin, bone morphogenetic protein, brain-derived neurotrophic factor, BRAK, transforming growth factor beta, and tumor necrosis factor. Exemplary matrix factors include, but are not limited to, gelatin, fibronectin, elastin, tenacin, laminin, vitronectin, polypeptides, heparan sulfate, chondroitin, chondroitin sulfate, keratan, keratan sulfate, dermatan sulfate, carrageenan, heparin, chitin, chitosan, alginate, agarose, agar, cellulose, methyl cellulose, carboxyl methyl cellulose, and glycogen. When the cell tissue gel contains gelatin, its concentration can range from 0.01-100 mg/ml (e.g., 1 mg/ml). Preferably, the collagen and hyaluronan concentrations in this gelatin-containing gel are 6-40 mg/ml and 0.2-20 mg/ml, respectively.

The present invention also features a method of delivering cells (e.g., stem cells) into a subject, including (i) providing a cell implant containing the cell tissue gel described above, in which cells grow, and (ii) placing the cell implant in a site of the subject. Also within the scope of this invention is use of the cell tissue gel in manufacturing a cell implant used in cell delivery.

The details of one or more embodiments of the invention are set forth in the description below. Other features or advantages of the present invention will be apparent from the following detailed description of an example and also from the appended claims.

DETAILED DESCRIPTION OF THE INVENTION

Described herein is a tissue gel containing collagen and hyaluronan at a weight ratio of 0.01-100 to 1, and optionally one or more other components such as a matrix factor, a bioactive agent, and a nutrient for cell growth.

Collagen

Any of the naturally-occurring collagens or their functional variants can be used for preparing the tissue gel of this invention. At the present time, at least 28 genetically distinct species of collagens have been discovered. Collagen can be easily isolated and purified from collagen-rich tissues such as skin, tendon, ligament, and bone of humans and animals. Methods for isolating and purifying collagen are well known in the art. (See, e.g., U.S. Pat. No. 5,512,291; US Patent Publication 20040138695; Methods in Enzymology, vol. 82, pp. 33-64, 1982; The Preparation of Highly Purified Insoluble Collagen, Oneson, I., et al., Am. Leather Chemists Assoc., Vol. LXV, pp. 440-450, 1970; U.S. Pat. No. 6,090,996). Collagen can also be prepared by recombinant technology, such as those described by Advanced Tissue Sciences (La Jolla, Calif.) or purchased from various venders (e.g., Fibrogen; South San Francisco, Calif.). One example follows. Bovine deep flexor tendons, with fat and fascia removed, are washed with water, frozen, and sliced into 0.5 mm slices with a slicer. A suitable amount of the sliced tendons is first extracted with 50 ml of water at room temperature for 24 hours. The water-soluble fraction is discarded and the sliced tendons are then extracted with an acidic solution (e.g., 0.2 N HCl) at a suitable temperature (e.g., room temperature) for a suitable period of time (e.g., 12-24 hours). The HCl solution is discarded; the tendons rinsed with water to remove the residual acid. The rinsed tendons are then extracted with a basic solution (e.g., 0.75 M NaOH) at a suitable temperature (e.g., room temperature) for a suitable period of time (e.g., 12-24 hours). After discarding the basic solution, the sliced tendons are neutralized with an acidic solution (e.g., 0.1 N HCl) to a pH of 4-7 (e.g. 5) followed by repetitive washes with water to remove the residual base in the tendons. The tendons are then defatted with an alcohol (e.g., isopropanol) for a sufficient period (e.g., 16 hours) at room temperature. The extractant is decanted and the tendons are further extracted with an alcohol (e.g., isopropanol) for a suitable period (e.g., 12-24 hours) at room temperature to form a collagen-containing solution, which can be dried under a clean hood. The collagen powder thus formed can be dispersed in an acidic solution (e.g., 0.5 M or 0.25 M acetic acid) in the presence of a proteolytic enzyme (e.g., trypsin or pepsin) and incubated at 4° C. for a suitable period. The mixture is then filtered through a 100 mesh stainless steel mesh filter and the solubilized collagen can be precipitated with a 5% NaCl solution. The precipitated collagen can be redissolved in the acidic solution described above and the solution thus formed can be filtered through a 100 mesh stainless steel mesh filter to eliminate non-solubilized particles. The collagen solution is then dialyzed with distilled water to remove the acid.

Hyaluronan

The term "hyaluronan" refers to a naturally-occurring anionic, non-sulfated glycosaminoglycan including repeated disaccharide units of N-acetylglucosamine and D-glucuronic acid, and its derivative. Naturally-occurring hyaluronan (also known as hyaluronic acid or hyaluronate) can be isolated from its natural sources, e.g., capsules of Streptococci, rooster comb, cartilage, synovial joints fluid, umbilical cord, skin tissue and vitreous of eyes, via conventional methods. See, e.g., Guillermo Lago et al. Carbohydrate Polymers 62(4): 321-326, 2005; and Ichika Amagai et al. Fisheries Science 75(3): 805-810, 2009. Alternatively, it can be purchased from a commercial vendor, e.g., Genzyme Corporation, Lifecore Biomedical, LLC and Hyaluron Contract Manufacturing. Derivatives of naturally-occurring hyaluronan include, but are not limited to, hyaluronan esters, adipic dihydrazide-modified hyaluronan, hyaluronan amide products, crosslinked hyaluronic acid, hemiesters of succinic acid or heavy metal salts thereof hyaluronic acid, partial or total esters of hyaluronic acid, sulphated hyaluronic acid, N-sulphated hyaluronic acid, and amines or diamines modified hyaluronic acid. They can be obtained by chemically modifying one or more of its functional groups (e.g., carboxylic acid group, hydroxyl group, reducing end group, N-acetyl group). A carboxyl group can be modified via esterification or reactions mediated by carbodiimid and bishydrazide. Modifications of hydroxyl groups include, but are not limited to, sulfation, esterification, isourea coupling, cyanogen bromide activation, and periodate oxidation. A reducing end group can be modified by reductive amination. It also can be linked to a phospholipid, a dye (e.g., a fluorophore or chromophore), or an agent suitable for preparation of affinity matrices. Derivatives of naturally-occurring hyaluronan can also be obtained by crosslinking, using a crosslinking agent (e.g., bisepoxide, divinylsulfone, biscarbodiimide, small homobifunctional linker, formaldehyde, cyclohexyl isocyanide, and lysine ethyl ester, metal cation, hydrazide, or a mixture thereof) or via internal esterification, photocross-linking, or surface plasma treatment.

Nutrient for Cell Growth

The term "nutrient" refers to a source of nourishment essential for cell growth. It can be amino acid, vitamin, mineral, carbon source (e.g., glucose), fatty acid, or a mixture thereof. In one example, the nutrient used in the tissue gel of this invention is a cell growth medium, e.g., Minimum Essential Medium, Basal Medium Eagle, Dulbecco's Modified Eagle's medium, Ham's Nutrient Mixtures F-10 or F-12, Medium 199, RPMI medium, Ames' Media, BGJb Medium (Fitton-Jackson Modification), Click's Medium, CMRL-1066 Medium, Fischer's Medium, Glascow Minimum Essential Medium, Iscove's Modified Dulbecco's Medium, L-15 Medium, McCoy's 5A Modified Medium, NCTC Medium, Swim's S-77 Medium, Waymouth Medium, or William's Medium E.

Bioactive Agent

Any agent (e.g., peptide, polypeptide, oligosaccharide, polysaccharide, or small molecule) that improves cell viability, promotes cell proliferation, or induces cell differentiation can be used in making the tissue gel of this invention. In one example, the bioactive agent is a growth factor, such as epidermal growth factor, fibroblast growth factor, vascular endothelial growth factor, connective tissue growth factor, platelet-derived growth factor, insulin-like growth factor, nerve growth factor, hepatocyte growth factor, colony-stimulating factors, stem cell factor, serotonin, and von Willebrand factor, transforming growth factor, keratinocyte growth factor, granulocyte colony-stimulating factor, granulocyte/macrophage colony stimulating factor, glial derived neurotrophic factor, ciliary neurotrophic factor, endothelial-monocyte activating polypeptide, epithelial neutrophil activating peptide, erythropoietin, bone morphogenetic proteins, brain-derived neurotrophic factor. In another example, the bioactive agent is a cytokine or chemokine, including, but are not limited to, IL-2, breast-expressed chemokine (e.g., BRAK), kidney-expressed chemokine (e.g., CXCL14). The bioactive agent can also be a cell differentiation factor, such as dexamethasone, sodium pyruvate, ascorbic acid-2-phosphate, retinoic acid, proline, insuline, transferrin, selenous acid, linoleic acid, and bovine serum albumin, and TGF-β3. In a preferred example, the differentiation factor is a compound that promotes chondrogenesis of mesenchymal stem cells (see those disclosed in U.S. Pat. No. 5,908,784), osteogenesis (e.g., dexamethasone, ascorbic acid, β-glycerol phosphate), adipogenesis (e.g., insulin, isobutyl-methyl xanthine, dexamethasone, indomethacin), cardiomyogenic differentiation (e.g., activin A, BMP-4), endothelial cell differentiation (e.g., EBM-2, dexamethasone, and VEGF), smooth muscle cell differentiation (e.g., PDGF-BB), neural induction (e.g., bFGF, EGF, and B27 supplement, DMSO, butylated hydroxyanisole, forskolin, valproic acid, KCl, K252a, and N2 supplement) and endodermal lineage differentiation (e.g., dexamethasone, HGF, and FGF-4). The bioactive agent can also be a Chinese herbal medicine or an active ingredient thereof.

Matrix Factor

A matrix factor is a compound that helps retain cells at an implantation site. It can be an extracellular factor found in the extracellular matrix. Examples are, but are not limited to, gelatin, fibronectin, elastin, tenacin, laminin, vitronectin, polypeptides, heparan sulfate, chondroitin, chondroitin sulfate, keratan, keratan sulfate, dermatan sulfate, carrageenan, heparin, chitin, chitosan, alginate, agarose, agar, cellulose, methyl cellulose, carboxyl methyl cellulose, glycogen and derivatives thereof. In addition, the matrix factor can be fibrin, fibrinogen, thrombin, and polyglutamic acid, a synthetic polymer (e.g., acrylate, polylactic acid, polyglycolic acid, or poly(lactic-co-glycolic acid), or a cross-linking agent (e.g., genipin, glutaraldehyde, formaldehyde, or epoxide). It is preferred that the matrix factor used in the tissue gel described herein has a high molecular weight so as to increase the viscosity of the gel.

Preparation of Tissue Gels with Cell Embedded

The tissue gel described herein can be prepared by mixing all of its components mentioned above at a desired weight ratio and keeping the mixture under suitable conditions to allow gel formation. To prepare a cell-embedded gel, desired cells can be mixed with the gel components prior to gel formation. The cells can be stem cells obtained from a mammal (e.g., bovine, porcine, murine, equine, canine, feline, ovine, simian, and human). Examples are, but are not limited to, placenta-derived stem cells, bone marrow-derived stem cells, stromal cells (e.g., adipose-derived stromal cells), mesenchymal stem cells, tissue progenitor cells, blast cells, or fibroblasts.

The tissue gel thus prepared, with cells embedded, can be implanted to a desired site for tissue repair and other therapeutic purposes.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Stem Cell Viability in Tissue Gels Containing Collagen and Hyaluronan

Chorionic villi were obtained from full-term human placentas, mechanically minced, and then digested with colagenase to obtain a material containing placenta-derived mesenchymal stem cells. The material was passed through sieves having mesh sizes of 300-, 100-, and 37-μm sequentially and then subjected to percoll density gradient centrifugation to collect stem cells. The cells were suspended in 2×low glucose Dulbecco's Modified Eagle's Medium (Gibco BRL, Life Technologies) supplemented with 20% fetal bovine serum and 200 U/ml gentamycin, at a concentration of $10^5$-$10^7$ cells/ml, and mixed with various amounts of hyaluronan to form a suspension. Collagen, obtained from porcine dermis, was dissolved in 0.01 N HCl to form a collagen solution having a pH of 4-7. The collagen solution was mixed with the stem cell-containing suspension at an equal volume to form a mixture having 6 mg/ml of collagen and 0.05 mg/ml, 0.2 mg/ml, or 0.5 mg/ml of hyaluronan, or 9 mg/ml of collagen and 0.2 mg/ml of hyaluronan. Mixtures containing collagen at 6 mg/ml and 9 mg/ml and the same amount of stem cells were used as controls. Any of the above-described mixtures were kept at 37° C. of incubator for 30 minutes to allow collagen solidification so as to form a tissue gel embedded with stem cells. The tissue gel was cultured at 37° C. with 5% $CO_2$ supply for up to 14 days. Cell viabilities at different time point (e.g., day 1, day 7, and day 14) were examined by trypan blue staining. The results thus obtained are shown in Table 1 below.

As shown in Table 1, the weight ratio of collagen vs. hyaluronan in the tissue gel was critical for maintaining viability of the stem cells grown in the gel over time.

TABLE 1

Stem Cell Viability in Tissue Gels Containing Collagen and Hyaluronan

| Concentrations (mg/ml) | | Percentage of Viable Cells (%) | | |
|---|---|---|---|---|
| Collagen | Hyaluronan | Day 1 | Day 7 | Day 14 |
| 6 | 0 | 87.5 | 41.8 | 40.5 |
| 6 | 0.05 | 80 | 72.3 | 63.6 |
| 6 | 0.2 | 85.1 | 73.2 | 75.3 |
| 6 | 0.5 | 70.8 | 43.4 | 57.7 |
| 9 | 0 | 96.3 ± 3.4 | N.A. | 35.7 ± 0.3 |
| 9 | 0.2 | 93.8 ± 1.0 | N.A. | 72.7 ± 10.4 |

EXAMPLE 2

Stem Cell Viability in Tissue Gels Containing Collagen, Hyaluronan, and Gelatin The stem cell suspension and collagen solution described in Example 1 above were mixed at 1:1 by volume together with gelatin (2 or 10 mg/mL) to form stem cell-embedded tissue gels. Their final concentrations of collagen, hyaluronan, and gelatin are shown in Table 2 below.

The tissue gels were cultured at 37° C. with 5% $CO_2$ supply for up to 14 days. Cell viabilities at different time (e.g., day 1, day 7, and day 14) were examined as described in Example 1 above. Table 2 below lists the percentages of viable cells grown in the tissue gels described above.

TABLE 2

Stem Cell Viability in Tissue Gels Containing Collagen, hyaluronan, and Gelatin

| Concentrations (mg/ml) | | | Percentage of Viable Cells (%) | | |
|---|---|---|---|---|---|
| Collagen | hyaluronan | Gelatin | Day 1 | Day 7 | Day 14 |
| 6 | 0 | 1 | 93.1 | 43.5 | 54.7 |
| 6 | 0.05 | 1 | 87.3 | 76.8 | 49.1 |
| 6 | 0.2 | 1 | 90.2 | 71.4 | 78 |
| 6 | 0.5 | 1 | 58.5 | 55.6 | 42.4 |
| 6 | 0 | 5 | 80 | 22.1 | 41.5 |
| 6 | 0.05 | 5 | 93.2 | 40 | 46.3 |
| 6 | 0.2 | 5 | 71.9 | 42.9 | 44.4 |
| 6 | 0.5 | 5 | 44.4 | 19.1 | 33.1 |
| 9 | 0.2 | 1 | 98.0 ± 0.4 | N.A. | 47.8 ± 6.5 |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A cell-embedded gel, the cell-embedded gel comprising collagen and hyaluronan at a weight ratio of 30-45:1, stem cells, and one or more optional components selected from the group consisting of a matrix factor, a nutrient, and a bioactive agent, wherein the cell-embedded gel is produced by mixing the collagen, the hyaluronan, the stem cells, and the one or more optional components to obtain a mixture, and allowing the collagen to solidify to form a gel embedded with the stem cells, wherein the viability of the thus embedded stem cells at day 14 of culture is greater than that of stem cells embedded in a control gel containing collagen but not hyaluronan.

2. The cell-embedded gel of claim 1, wherein the mixture contains 6-9 mg/ml of collagen and 0.2 mg/ml of hyaluronan.

3. The cell tissue gel of claim 1, wherein the nutrient is a cell culture medium.

4. The cell-embedded gel of claim 1, wherein the bioactive agent is a growth factor selected from the group consisting of epidermal growth factor, fibroblast growth factor, vascular endothelial growth factor, connective tissue growth factor, platelet-derived growth factor, insulin-like growth factor, nerve growth factor, hepatocyte growth factor, colony-stimulating factor, stem cell factor, keratinocyte growth factor, granulocyte colony-stimulating factor, granulocyte macrophage colony-stimulating factor, glial derived neurotrophic factor, ciliary neurotrophic factor, endothelial-monocyte activating polypeptide, epithelial neutrophil activating peptide, erythropoietin, bone morphogenetic protein, brain-derived neurotrophic factor, BRAK, transforming growth factor beta, and tumor necrosis factor.

5. The cell-embedded gel of claim 1, wherein the matrix factor is selected from the group consisting of gelatin, fibronectin, elastin, tenacin, laminin, vitronectin, polypeptides, heparan sulfate, chondroitin, chondroitin sulfate, keratan, keratan sulfate, dermatan sulfate, carrageenan, heparin, chitin, chitosan, alginate, agarose, agar, cellulose, methyl cellulose, carboxyl methyl cellulose, and glycogen.

6. The cell-embedded gel of claim 5, wherein the one matrix factor is gelatin, the mixture containing 1 mg/ml of gelatin, 6 mg/ml of collagen, and 0.2 mg/ml of hyaluronan.

7. A method of delivering stem cells into a subject, comprising:
   providing a cell implant containing the cell-embedded gel of claim 1, in which stem cells grow, and
   placing the implant in a site of the subject.

8. The cell tissue gel of claim 1, wherein the weight ratio of collagen to hyaluronan is 30 or 45:1.

9. The cell-embedded gel of claim 8, wherein the mixture consists of the a collagen solution in HCl, hyaluronan, stem cells and a cell culture medium.

* * * * *